United States Patent

Del Bon et al.

[11] Patent Number: 5,571,217
[45] Date of Patent: Nov. 5, 1996

[54] PROTECTIVE ASSEMBLY FOR THE PROTECTION OF THE HUMAN HEAD

[75] Inventors: Francesco Del Bon, Aarburg; Christoph Lutz, Maur, both of Switzerland

[73] Assignee: Optrel AG, Switzerland

[21] Appl. No.: 96,612

[22] Filed: Jul. 23, 1993

[30] Foreign Application Priority Data

Jul. 24, 1992 [DE] Germany .......................... 42 24 476.5

[51] Int. Cl.⁶ ........................................................ A61F 9/06
[52] U.S. Cl. ............................................................ 2/9; 2/8
[58] Field of Search ............................... 2/7, 8, 9, 10, 11, 2/410, 417, 418, 419, 420, 424

[56] References Cited

U.S. PATENT DOCUMENTS

| | | | |
|---|---|---|---|
| 2,283,120 | 5/1942 | Malcom | 2/8 |
| 2,320,244 | 5/1943 | Maillart | 2/8 |
| 2,658,200 | 11/1953 | Bowers, Sr. | 2/8 |
| 2,788,558 | 4/1957 | Bowers, Jr. | 2/8 |
| 2,973,522 | 3/1961 | Edwards et al. | 2/8 |
| 3,075,201 | 1/1963 | Lindblom | 2/8 |
| 3,430,263 | 3/1969 | Newcomb | 2/8 |
| 3,444,560 | 5/1969 | Northup, Jr. | 2/8 |
| 3,696,442 | 10/1972 | Amundsen et al. | 2/8 |
| 4,427,960 | 2/1981 | Nava | 2/424 |
| 4,464,800 | 8/1984 | Edwards | 2/8 |

*Primary Examiner*—Michael A. Neas
*Attorney, Agent, or Firm*—Tarolli, Sundheim, Covell, Tummino & Szabo

[57] ABSTRACT

A protective assembly for the head which has a circular support structure adapted to be connected to the head of the person wearing the protective assembly. A protective visor is pivotally connected to the support structure to be swiveling from a lower operating position to an upper resting position. Mechanisms, having actuating members, are provided for adjusting and fixing the position of the visor in the viewing direction and in the lower operating position. All of the actuating members are located at the outer side of the protective assembly and the visor respectively, such that they can be activated while the protective assembly is being worn.

22 Claims, 7 Drawing Sheets

5,571,217

PROTECTIVE ASSEMBLY FOR THE PROTECTION OF THE HUMAN HEAD

FIELD OF THE INVENTION

The present invention refers to a protective assembly for the protection of the human head from external detrimental effects, comprising a support structure adapted to be connected to the head of the person wearing the protective assembly, a visor exerting the desired protective function, the visor means being pivotally connected to the support structure to be swiveling from a lower operative position to an upper rest position, and means for adjusting and fixing the position of the visor in the viewing direction and in the lower operative position.

PRIOR ART

Known in the prior art is a protective assembly for the protection of the human head in the form of a welder's helmet for the protection of the eyes of the welder upon the occurrence of a welding arc which is, as obvious to any person skilled in the art, of a very high light intensity. In such a helmet, the support structure of the helmet comprises a forehead tape portion which is adjustable in its length as well as a supporting ring member surrounding the forehead tape member with a certain distance and being made of a upright positioned tape profile. The supporting ring member is provided with a collar to increase the shape stability thereof. The forehead tape member as well as two cross wisely running head tape portions made of textile material are connected to the supporting ring member. Furthermore, a visor member is connected to the aforementioned supporting ring member.

For fixing these parts and elements to the supporting ring member, plug-in connections are provided which are not releasable during the use of the protective assembly. Additionally, as connecting means between forehead tape member and supporting ring member, radially resilient tab members are inserted. In the region of the lateral portions of the supporting ring member, bearing members are provided for receiving each a laterally protruding pivot pin member for the swiveling mounting of the visor member. The visor member comprises two lateral portions which have port-like apertures penetrated by the aforementioned pivot pins.

In order to fix or preset the operative position of the visor member with reference to the support structure, i.e. the lower position of the visor member, a stop member assembly is provided. Thereby, the one lateral portions of the visor member comprises at its inner surface a rib member serving as a fixed stop member, and the supporting ring member comprises an adjustable abutment member cooperating with the aforementioned rib member. The adjustable abutment member is located at the end of the one leg of a first-order lever, the other leg thereof being designed as a toothed segment.

The first-order lever is pivotally mounted between the lateral portion of the visor member and the supporting ring member by means of a threaded bolt, and the toothed leg of the lever cooperates with a correspondingly toothed portion of the related bearing member mentioned herein above. By varying the mutual engagement position between the teeth of the toothed leg of the lever and the teeth of the toothed portion of the bearing member, this stop member assembly and thereby the angle of the visor member with reference to the support structure may be adjusted. The toothed segment is elastically resiliently designed; in order to adjust the stop member assembly to change the tilting angle of the visor member, the toothed segment can be temporarily bent away from the toothed bearing member to disengage the toothings of these two members.

The forehead tape portion of the support structure of the known protective assembly is in the form of a stiff-elastic tape which ends comprise connecting means for closing the forehead tape portion to a loop having a desired length. These connecting means are realized such that the one end of the tape portion is provided with a number of holes arranged along a row in the longitudinal extension of the tape portion, and the other end is provided with a protruding pin adapted to engage one of the aforementioned holes if the two ends are arranged one in top of the other one.

Practice has shown that the means for adapting the helmet to the head of a particular person and, particularly, the means for adjusting the tilting angle of the visor are impractically designed and arranged in as much as they can be operated only if the helmet is removed from the head of the welder. The result is that, in many cases, a perfect adaptation of the helmet which is a need for a comfortable working can be effected only if the protective assembly is stepwisely adapted in a trial-and-error approach. It is self-understanding that this procedure takes a lot of time, particularly if one protective assembly has to be used by a number of different persons.

OBJECTS OF THE INVENTION

It is an object of the present invention to provide a protective assembly for the protection of the human head from external detrimental effects which avoids the disadvantages of the protective assemblies known in the prior art.

Particularly, it is an object of the present invention to provide a protective assembly for the protection of the human head from external detrimental effects which can be adapted to the head of a person wearing the protective assembly and which can be adjusted in its operative position, thereby avoiding the need to repeatedly remove the protective assembly from the head, to adjust it and to place it again on the head.

SUMMARY OF THE INVENTION

To meet these and other objects, the present invention provides a protective assembly for the protection of the human head from external detrimental effects. The protective assembly comprises a support structure adapted to be connected to the head of the person wearing the protective assembly, a visor member exerting the desired protective function, the visor means being pivotally connected to the support structure to be swiveling from a lower operative position to an upper rest position, and means for adjusting and fixing the position of the visor member in the viewing direction and in the lower operative position.

The means for adjusting and fixing the position of the visor member includes actuating members for the operation of the means for adjusting and fixing the position of said visor means, all these actuating members being located at the outer side of the protective assembly and the visor member, respectively, such that they can be actuated in the operative position of the protective assembly to adjust and fix the position of the visor member in the viewing direction and in the lower operative position.

According to a preferred embodiment of the invention, in which the support structure comprises a stiff-elastic forehead tape portion as known in the art, the visor member is fixed immediately to the forehead tape portion; thereby, simple design prerequisites are given which can easily be met.

If the visor member comprises, as known in the art, two lateral portions being in operative connection with the support structure, and if each of the lateral portions are connected to the support structure by means of a releasable screw connection operating as a friction-clutch member, the forehead portion of the support structure can be provided with a radially outwardly protruding tape section located in the temple region of the support structure which serves as a basis portion for the determination of the releasable screw connection.

Thereby, each of the radially outwardly protruding tape sections of the support structure and the lateral portions of the visor member overlapping the tape sections each can comprise a port-like aperture for receiving a threaded bolt forming the pivot axis for the visor. One of the port-like apertures, on each side of the visor, is in the shape of a longitudinal slit extending essentially parallel to the direction of viewing of the person wearing the protective assembly.

In a further development of this embodiment, each of the longitudinal slits can comprise, along its longitudinal extension, a plurality of snap-in recesses adapted to cooperate with an actuating knob member. The actuating knob member preferably is located on the threaded bolt at the outside of the lateral portions of the visor in order to enable the visor to positively fix the position of the visor with reference to the support structure in one of several predetermined positions defined by the snap-in recesses.

According to another embodiment, the port-like aperture can be in the shape of a longitudinal slit which is located in the radially outwardly protruding tape section of the support structure.

In any case, there is provided a stop member assembly for determining the lower operative position of the pivotal visor member. The stop member assembly normally comprises a fixed stop member and an adjustable abutment member cooperating with the fixed stop member. The fixed stop member is located at one of the radially outwardly protruding tape section of the forehead portion of the support structure and the adjustable abutment member is located at the inner side of the related lateral portion of the visor member facing the outer side of the aforementioned lateral portion of the visor member. Thereby, the adjustable abutment member is displaceable along a longitudinally extending path and provided with a stop edge running crosswise to the longitudinally extending path.

The adjustable abutment member can be fixed to the lateral portion of the visor member by means of a releasable screw connection comprising a threaded bolt penetrating a port-like aperture provided in the lateral portion of the visor member as well as an actuating knob member received on the threaded bolt at the outer side of the lateral portion of the visor member.

According to a first possibility, the threaded bolt is fixedly connected to the related lateral portion of the visor member, the related lateral portion of the visor member comprising a longitudinal slit along which the threaded bolt can be infinitely variably displaced and the threaded bolt being received in the longitudinal slit such that the threaded bolt cannot be rotated.

According to a second possibility, the position of the threaded bolt can be fixed in the port-like aperture provided in the lateral portion of the visor member, whereby the adjustable abutment member comprises a longitudinal slit by means of which the abutment member is linearly displaceably and non-rotatably received on the threaded bolt. Thereby, the adjustable abutment member includes spring means for forcing the adjustable abutment member against the fixed stop member once the connection between the adjustable abutment member and the fixed stop member is released.

According to a still further possibility, the position of the threaded bolt can be fixed with reference to the port-like aperture in the lateral portion of the visor member whereby the adjustable abutment member is connected to the threaded bolt by means of a friction-clutch and to the lateral portion of the visor member by means of a positively engaging clutch member which can be disengaged by axially displacing the threaded bolt.

In any case, the abutment and stop member means and the related actuating means preferably are located away from the ear portion of the support structure.

The protective assembly according to the invention further may comprise adjustment means for adapting the size of the support structure to the size of the head of the person wearing the protective assembly. These adjustment means comprise a self-locking adjustment assembly adjustable in the operative position of the protective assembly and adapted to adjust the circumferential dimension of the forehead tape portion of the support structure. Preferably, the self-locking adjustment assembly for the adjustment of the forehead tape portion of the support structure is located at the neck portion of the latter.

To easily and reliably realize such a self-locking adjustment assembly, the forehead tape portion of the support structure can comprise two free ends provided with a longitudinal slot, one of the edges of each slot being provided with a train of gears whereby the train of gears of the one slot is located on the opposite side as compared to the train of gears provided on the other slot if the two free ends are placed one above the other. Further provided is a clasp member surrounding the two free ends of the forehead tape portion, the clasp member comprising a gear wheel member rotatable about an axis, located in the interior of the clasp member and engaging the two train of gears provided along the one edge of each two slots. Thereby, the clasp member comprises a friction-clutch member hampering the rotational movement of the gear wheel member as well as an actuating knob fixed to the outer side of the axis of the gear wheel member.

BRIEF DESCRIPTION OF THE DRAWINGS

In the following, some embodiments of the apparatus according to the invention will be described, with reference to the accompanying drawings, in which.

DETAILED DESCRIPTION OF THE PREFERRED EMBODIMENTS

Figure 4:
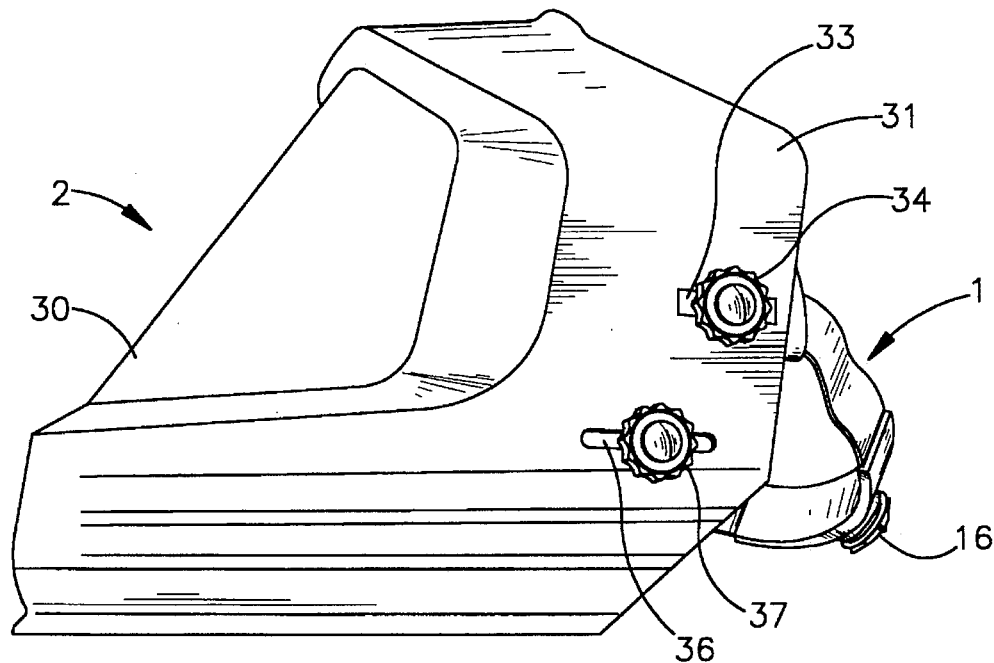
FIG. 4 shows a lateral view of a complete protection assembly incorporating a support structure according to FIG. 1.

As can be seen in FIG. 4, the protection assembly according to the invention essentially comprises a support structure 1 and a visor member 2 connected to the support structure 1 such that it can be tilted around a horizontally extending axis from a closed, operative position to an open, inoperative position. The main or essential part of the support structure 1 is constituted by a support framework 3 which is shown in FIG. 1 in its assembled operative condition.

Figure 1:
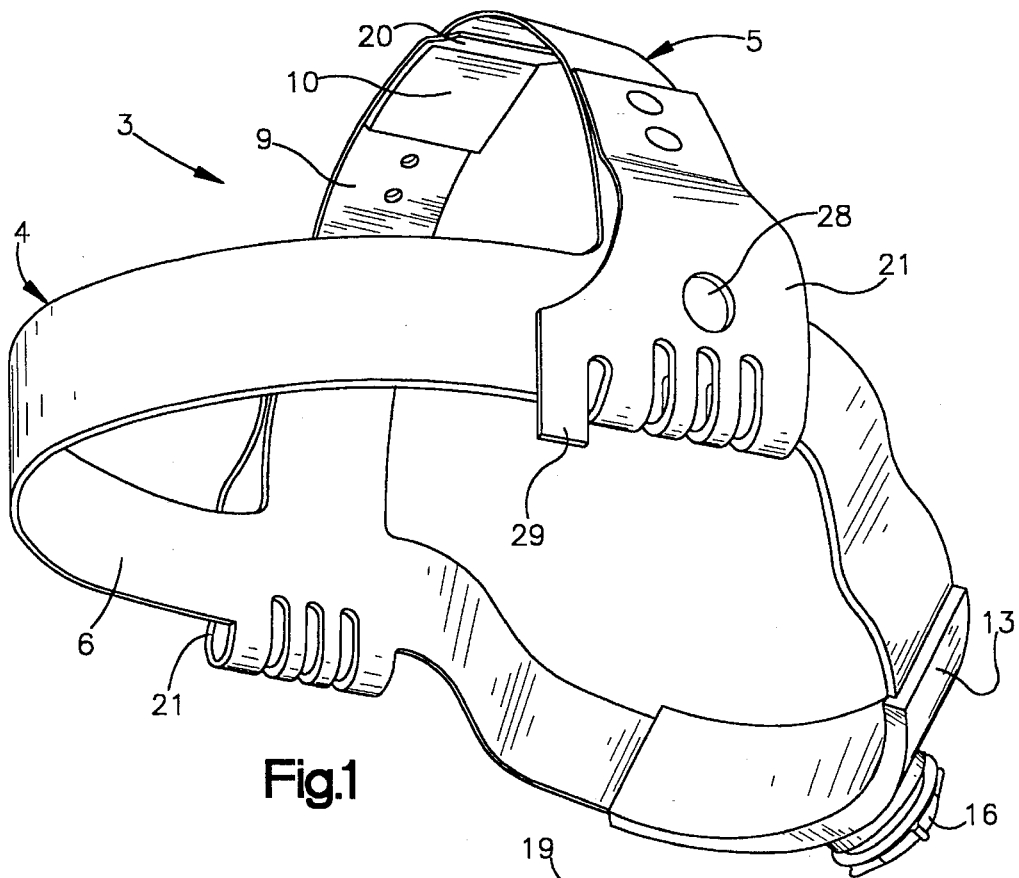
FIG. 1 shows a perspective view of a support framework being part of the support structure of the apparatus according to the invention.
Figure 2:
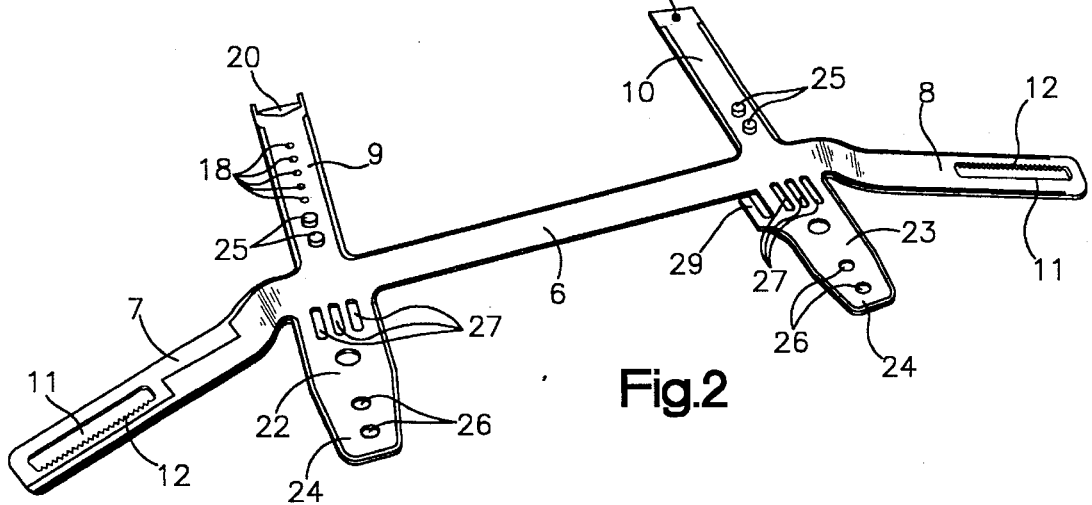
FIG. 2 shows a development of the tape sections constituting the support framework according to FIG. 1.

The support framework 3 according to FIG. 1 is made of a compact material, preferably of a plastic material like polyethylene, in one part and comprises a forehead tape portion 4 as well as a cross-tape member portion 5 running perpendicularly to the forehead tape portion 4. The basic structure for forming the support framework 3 is a flat tape member incorporating stiff-elastic tape portions, as shown in FIG. 2. Thereby, an elongate tape portion 6 forms the annular forehead tape 4, after it has been bent into an annular shape whereby the two end portions 7 and 8 thereof are connected together. The cross-tape member 5 is formed by bending the two cross-wisely protruding tape portions 9 and 10 and by connecting together their free end portions. As shown in FIG. 2, the tape portions 6, 9 and 10 are reinforced along their edges.

Figure 3:
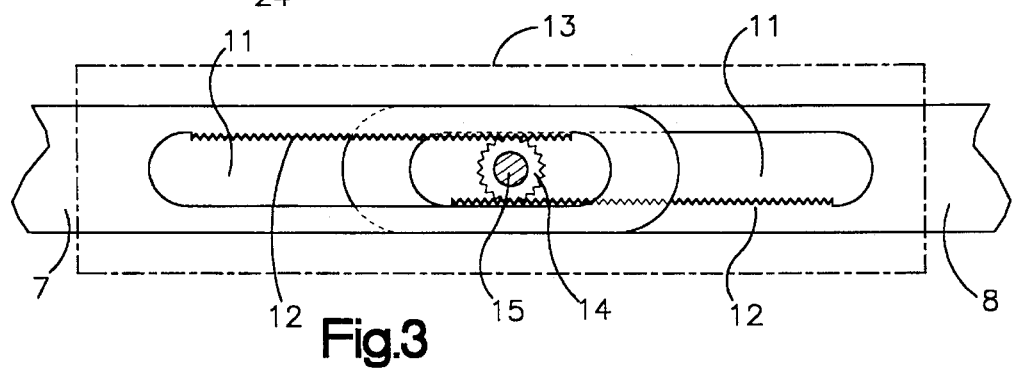
FIG. 3 shows a schematic detailed view of a clasp member provided on the forehead tape section.

The free ends of the tape portions are provided with connection means in order to close the forehead tape portion 4 and the cross-tape 5 in a desired length. As far as the forehead tape portion 4 is concerned, the two free ends 7 and 8 of the tape portion 6 constituting the forehead tape 4 each comprises a slot-shaped aperture 11 running along the longitudinal extension of the tape portion. One lateral edge of each slot-shaped aperture 11 is provided with a train of gears 12. Thereby, the train of gears 12 of the two slot-like apertures are located at opposite sides of the slot-like apertures such that the train of gears 12 face each other as soon as the two tape portions 7 and 8 are positioned one on the other one (FIG. 3).

Further, there is provided a clasp member 13 surrounding the tape end portions 7 and 8 forming the neck portion of the forehead tape 4. The clasp member 13 comprises a gear wheel 14 engaging the train of gears 12 provided on the two tape end portions 7 and 8 as well as a friction-clutch member (not shown). The gear wheel 14 is sited on an axis 15, the end thereof being provided with an actuating knob 16 for manually rotating the gear wheel 14. By operating the actuating knob 16, the two tape end portions 7 and 8 are continuously displaced in the direction of their longitudinal extension; if the gear wheel 14 is rotated in clockwise direction, the forehead tape is shortened, and if the gear wheel 14 is rotated in counter-clockwise direction, the forehead tape 4 is lengthened. Due to the provision of the friction-clutch member, the adjusted length of the forehead tape 4 is maintained. Without operating the actuating knob 16, the friction-clutch member is released only in such a case if external forces act onto the forehead tape portion 4 to such an extent that the safety of the person wearing the head protection assembly could be impaired.

In order to enable the cross tape 5 to be closed, the one tape portion 9 thereof comprises a number of holes 18 arranged in longitudinal extension, and the other tape portion 10 is provided with a plug member 19 located at its free end. The two tape portions 9 and 10 lying one above the other one, the plug 19 is inserted into one of the holes 18 provided in the tape portion 9. Depending on the position of the selected hole 18, the length of the cross tape 5 can be adjusted. On order to prevent that this closure assembly can not be opened by accident, the free end of the tape portion 9 is provided with a loop portion 20 surrounding the other tape portion 10.

As can be further seen in FIGS. 1 and 2, the forehead tape portion 4 comprises two tape portions 21 radially protruding toward the outside of the support framework 3. These portions 21 are located at the temple region of the forehead tape 4 and are adapted to serve as connection members for fixing the visor 2 to the support structure 1. In the present example, the above-mentioned tape portion 21 are constituted each by a further tape section 22 and 23, respectively, which perpendicularly protrude from the tape portion 6 constituting the forehead tape portion 4 and which are bent outwardly and upwardly to form a loop as shown in FIG. 1.

The starting points of the tape portions 22 and 23 forming the outwardly protruding tape sections 21 and the starting points of the tape portions 9 and 10 forming the cross-tape member 5 are located at opposite positions at the edges of the forehead tape member 4, and the end portions 24 of the tape portions 22 and 23 are connected to the tape portions 9 and 10, respectively, forming the cross-tape member 5. For this purpose, the tape portions 9 and 10 each are provided with two pins 25 and the tape portions 22 and 23 each are provided with two holes 26 adapted to receive the aforementioned pins 25. In the region in which the tape portions 22 and 23 are bent, the cross sections thereof are reduced by the provision of apertures 27.

Each of the outwardly protruding tape portions 21 is provided with a port 28 adapted to receive connection members serving for the fixing of the visor 2 to the support framework 3. Furthermore the tape portion 23 is provided with a stop member 29 integrally formed to the tape portion 23, said stop member 29 serving for determining the lower position, i.e. the operative position of the visor 2. The above-mentioned connecting members and the stop member 29 will be further explained in detail hereinafter with reference to FIGS. 6 and 7.

The support framework 3 shown in FIG. 1 usually is further provided with upholstery means (not shown in the drawings), fixed to the inner surface of the forehead tape 4, extending over the length thereof to the end portions 7 and 8, and which also can cover portions of the cross-tape member 5.

Instead of the tape portions 22, 23 which are bent each to form a slope, the outwardly protruding tape portions can also be constituted by sloped tape portions integrally formed with the forehead tape 4.

Figure 5:
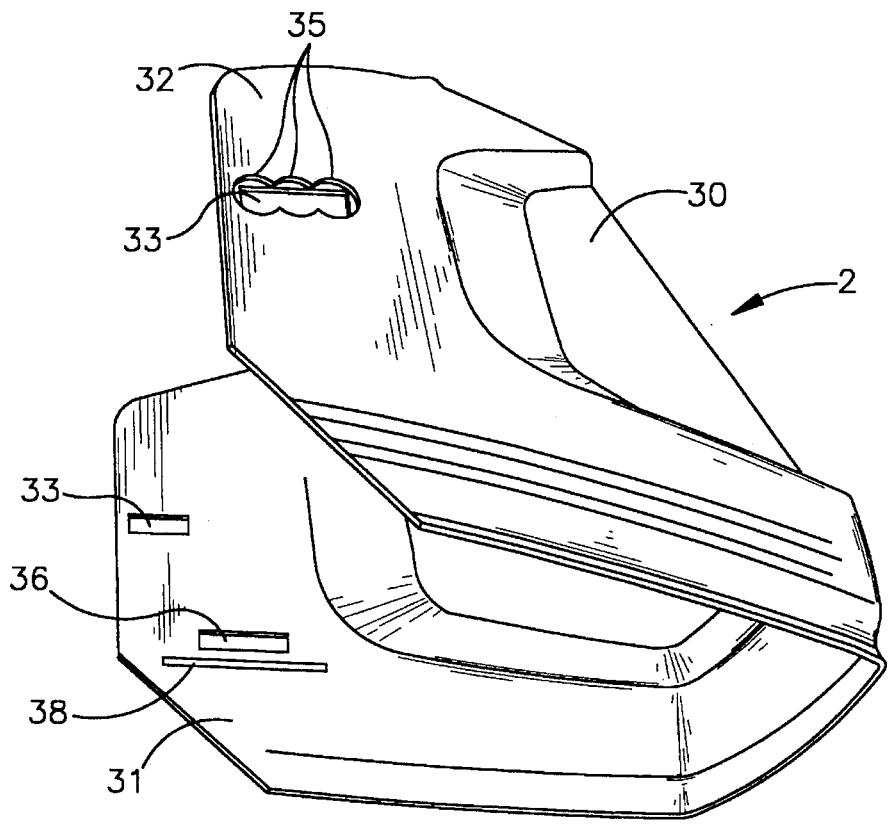
FIG. 5 shows a visor of the protection assembly according to FIG. 4, as viewed from the opposite side.

According to FIGS. 4 and 5 the visor 2 connected to the support structure 1 comprises a window 30 located at its front surface; for instance, such window 30 can be constituted by a filter member having variable transparency characteristics dependent on the amount of light falling on the window 30. Further, the visor 2 comprises two lateral portions 31 and 32 which are pivotally connected to the support framework 3 and which extend laterally to the back portion of the visor 2. Each of the portions 31 and 32 is provided with a longitudinal slit 33 through which a pivot pin (not shown in FIGS. 4 and 5) extends towards the outside. The pivot pin is inserted into the ports 28 of the tape portions 21 of the support framework 3. The two longitudinal slits 33 provide for a displacement of the visor 2 in the direction of viewing of the person wearing the protective assembly.

The pivot pin mentioned above is provided with a threaded portion adapted to receive an adjustment nut provided with a actuating knob 34 in order to fix the visor 2 in the selected displacement position. In the present example, three snap positions are provided in the direction of displacement of the visor 2; these snap positions are constituted by recesses 35 provided in the outward face of the lateral portions 31 and 32. Upon tightening the adjustment knob, a corresponding snap protrusion of the actuating knob 34 engages the above mentioned recesses.

In order to provide for an adjustment of the lower final pivot position, i.e. the operative position of the visor 2, there is provided a displaceable stop means not shown in FIG. 4 and 5 adapted to cooperate with a stop member 29 of the support framework 3 (FIG. 1) and which penetrates, e.g. by means of a further bolt, the longitudinal slit 36 provided at the left lateral portion 31 of the visor 2. The above-mentioned bolt can be fixed by an adjustment nut having a actuating knob 37. Below the said longitudinal slit 36 a strip member 38 is provided at the inner surface of the lateral portion 31 which serves for linearly guiding the above-mentioned stop member. Further details in this respect can be found hereinafter with reference to the detailed description of FIGS. 6 and 7.

Figure 6:
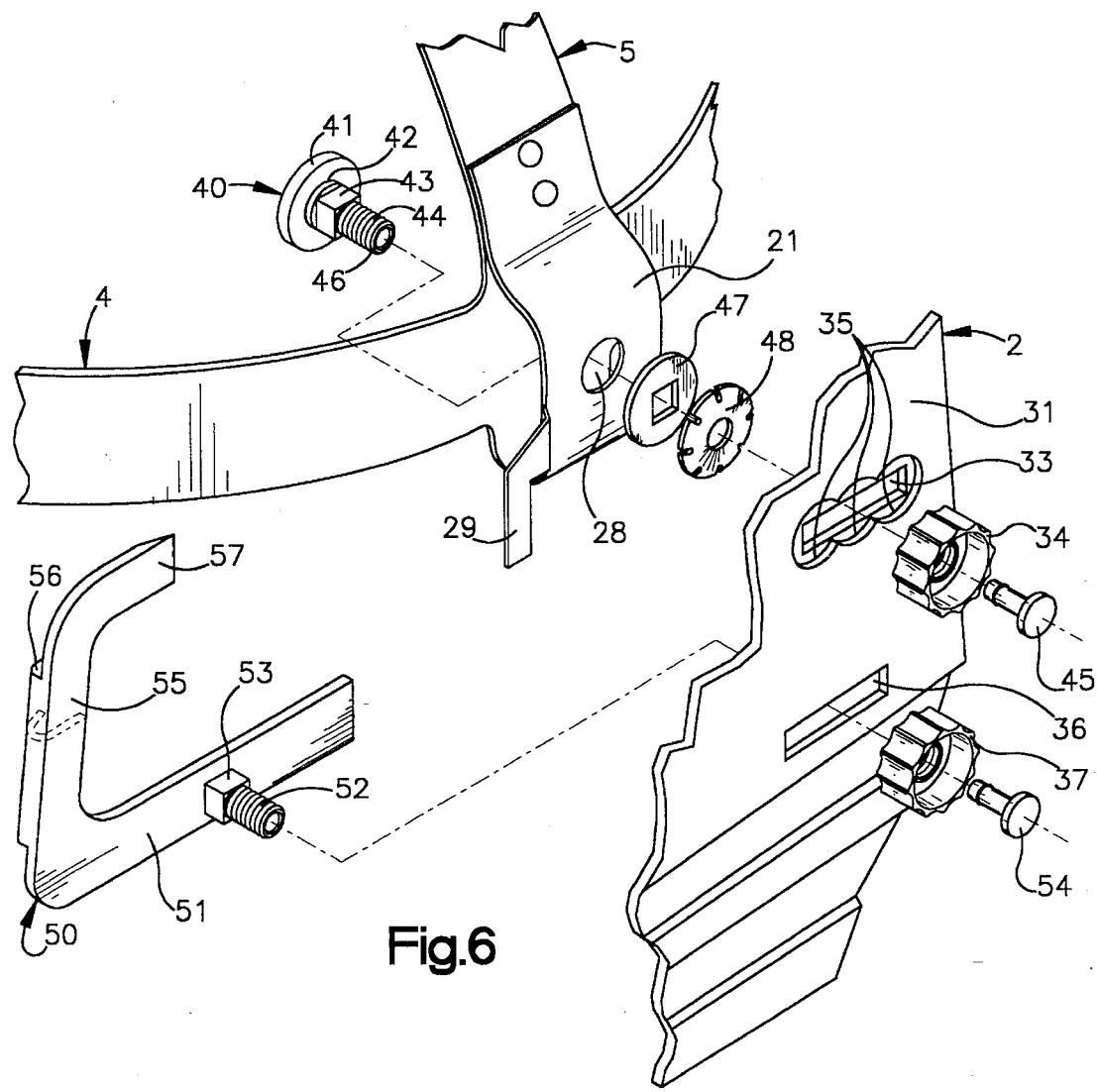
FIG. 6 shows an exploded view of some parts serving for the connection between the support structure and the visor.
Figure 7:
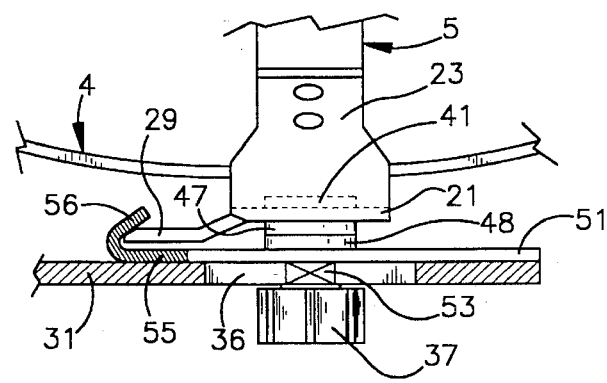
FIG. 7 shows a detailed sectional view of a stop assembly for a visor which can be tilted from an open position to an operative position.

In FIGS. 6 and 7, the same reference numbers are used for corresponding parts which also appear in the already discussed FIGS. 1–5. In the exploded view according to FIG. 6, the parts of the pivotal connection between the visor 2 and the support framework 3 can be seen. The pivot axis is constituted by a pivot pin 40 which is provided with a head portion 41, a cylindrical portion, a square cross-sectioned portion 43 and, at its end, a threaded portion 44. The pivot pin 40 is rotatably received in the circular port 28 of the tape portion 21 which is part of the forehead tape 4 by means of its cylindrical portion 42. The head portion 41 of the pivot pin 40 is located at that side of the forehead tape 4 which faces the tape portion 21. The square cross-sectioned portion 43 of the pivot pin is guided in the rectangular longitudinal slit 33 such to be longitudinally displaceable, but not rotatable. The threaded portion 44 of the pivot pin 40 receives the actuating knob 34 with its adjustment nut; a locking pin 45 engaging a central bore 46 of the pivot pin 40 ensures that the actuating knob 34 cannot be accidentally lost.

Between the tape portion 21 and the lateral portion 31 of the visor 2, which both portions are penetrated by the above-mentioned pivot pin 40, the said pivot pin 40 is provided with an intermediate washer 47 having a square bore and a spring washer 48. The latter one serves for securing the actuating knob 34 being engaged in one of the recesses 35 in its position during a pivotal movement of the visor 2.

In order to set the lower pivot position of the visor 2, i.e. the operational position thereof, there is provided a continuously adjustable stop member means including the already mentioned fixed stop member 29 as well as a displaceable abutment member 50 which can be fixed in a desired position. In the present example, the stop member means is located at the left-hand side of the visor 2; it is understood that it could be also located at the right-hand side thereof.

The abutment member 50 has the shape of a flat bow comprising a lower linear leg portion 51 engaging the above-mentioned strip member 38 (FIG. 5) and incorporating a fixedly connected threaded bow 52 with a square cross-sectioned portion 53. The square cross-sectioned portion 53 is guided in the rectangular longitudinal slit 36 of the lateral portion 31 of the visor 2 to be longitudinally displaceable, but not rotatable. The threaded bolt 52 is provided with the aforementioned actuating knob 37 with incorporated adjustment nut and is secured against loss with a locking pin 54. A further leg 55 of the abutment member 50 extending crosswise to the aforementioned leg 51 comprises a bent portion forming a hook 56 cooperating with the fixed stop member 29 as shown in FIG. 7. A further upper leg 57 runs in essentially parallel direction to the lower leg 51; the said upper leg serves to engage the outwardly protruding tape portion 21 upon a pivotal movement of the visor 2 from the upper rest position into the lower operational position; thereby, the hook 56 contacts with its opening the fixed stop member 29.

The length of the leg 51 of the adjustable abutment member 50 preferably is dimensioned such that the leg 51 covers the longitudinal slit 36 in the lateral portion 31 of the visor 2 in every displacement position of the abutment member 50 in order not to impair the protective function of the visor 2 by the presence of an aperture at this location.

Figure 8:
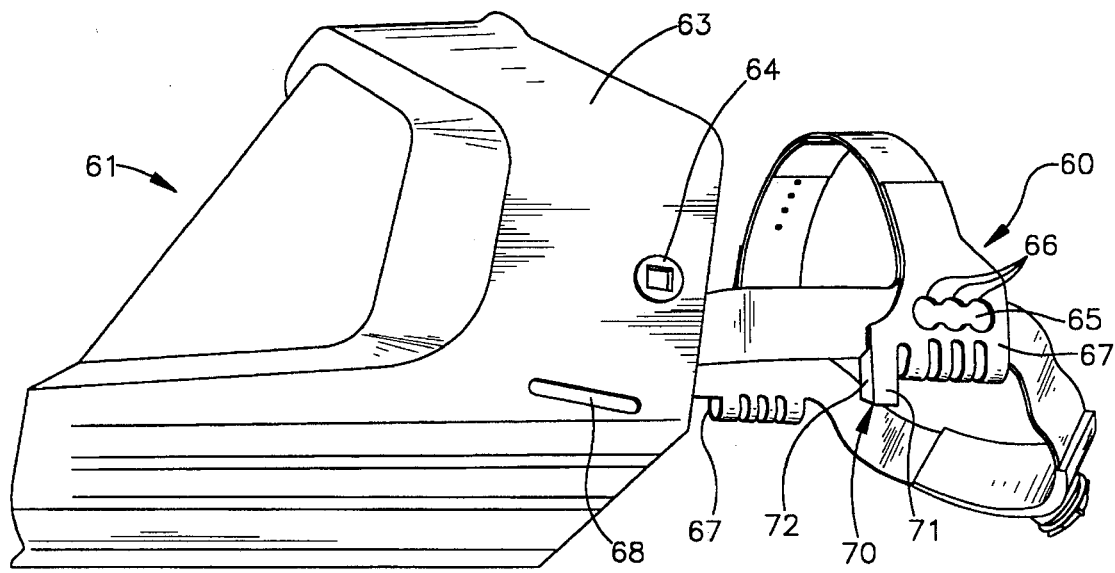
FIG. 8 shows a lateral view Of another embodiment of the apparatus according to the invention incorporating a different assembly for the longitudinal adjustment of the visor in a disassembled state.
Figure 9:
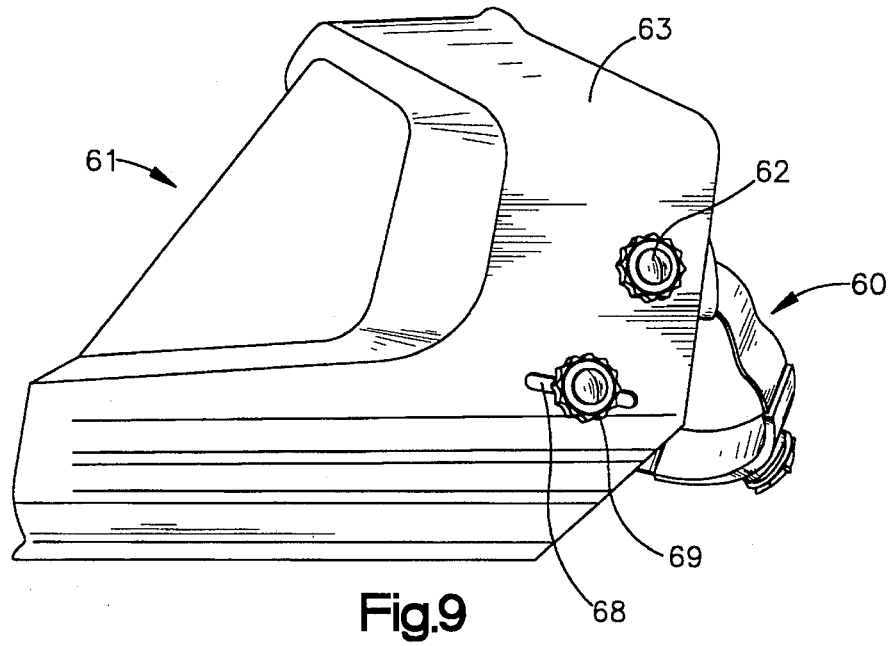
FIG. 9 shows a lateral view of another embodiment of the apparatus according to FIG. 8 incorporating a different assembly for the longitudinal adjustment of the visor in an assembled state.

The embodiment according to FIGS. 8 and 9 also shows a support structure 60 as well as a related visor 61; this embodiment differs from the one shown in FIGS. 4 and 5 by the fact that the pivot bolt provided with the adjustment knob 62 has a fixed position with reference to the lateral portion 63 of the visor 61 by means of a bearing bush 64. The longitudinal slit 65 with its snap-in portions 66 provided for the displacement of the visor 61 in the viewing direction is located, in this embodiment, in the outwardly protruding tape portions 67 of the support structure 60. In this manner, the need is removed to provide the lateral portions of the visor with a corresponding longitudinal slit, with the result that the protection effect of the visor is further improved due to the lack of additional apertures.

The longitudinal slit 68 for the displacement of the adjustable stop member with the adjustment knob 69 is, in this connection, less critical as is shown in FIG. 8. The adjustable stop member, not shown in FIG. 8, cooperates with a fixed abutment member 70 comprising a tape portion 71 integrally formed with the tape portion 67 of the support structure 60 as well as a land member 72 protruding radially inwardly from the longitudinal edge thereof.

Figure 10:
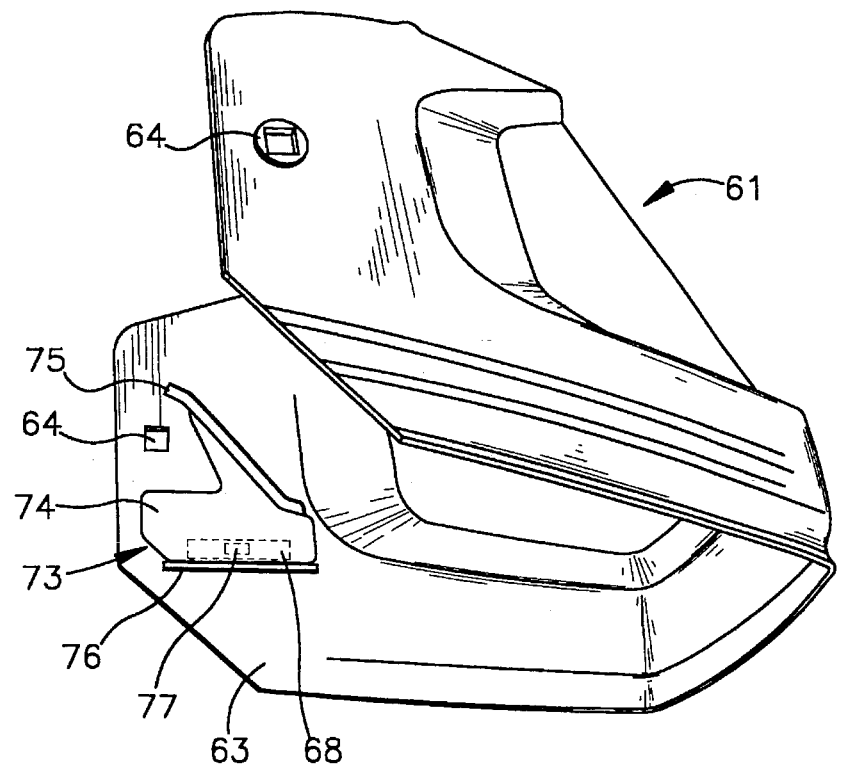
FIG. 10 shows a perspective view of the visor incorporating a still different embodiment of the stop assembly for the adjustment of the visor.
Figure 11:
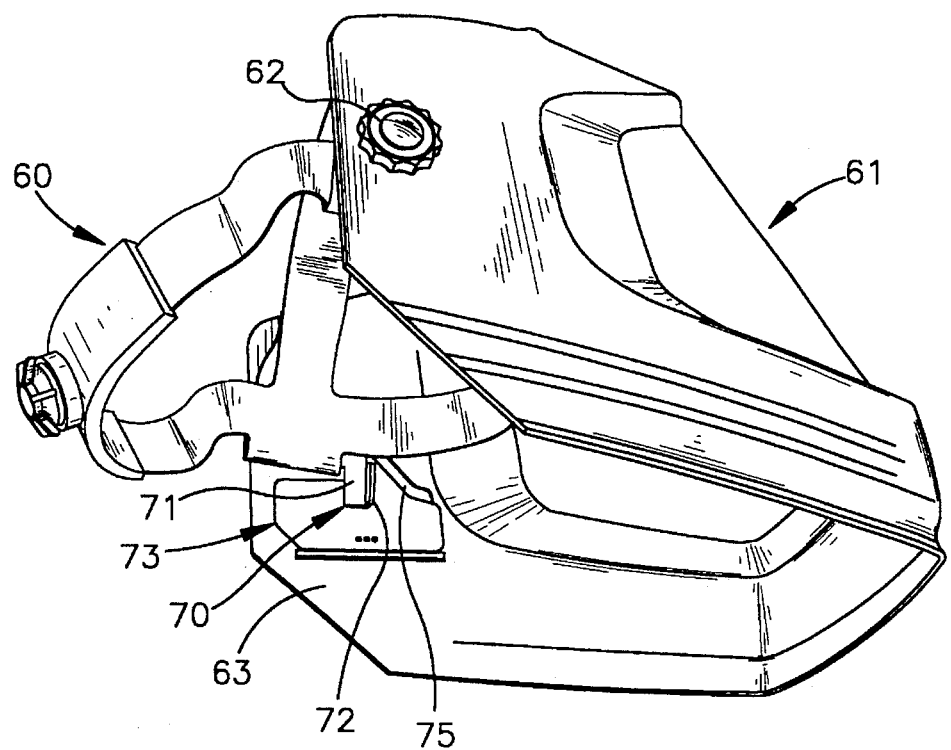
FIG. 11 shows a perspective view of the complete apparatus according to the invention incorporating the assembly for the longitudinal adjustment of the visor shown in FIG. 10.

An embodiment similar to the one shown in FIGS. 6 and 7, but incorporating abutment member means having a different stop member, is shown in FIGS. 10 and 11. All remaining parts of the embodiment according to FIGS. 10 and 11 are identical with the ones shown in FIGS. 8 and 9 and have the same reference numerals. The adjustable abutment member 73 comprises a plate-shaped portion 74 as well as stop edge 75 protruding in perpendicular direction from that plate-shaped portion 74. The above-mentioned stop edge cooperates with a fixed stop member 70. The plate-shaped portion 74 is longitudinally displaceably guided in a manner equal to the one explained in connection with FIGS. 6 and 7; thereby, the lateral portion 63 of the visor comprises a longitudinal slit 68 and a guiding strip member 76. Reference numeral 77 indicates a threaded bolt for fixing the adjustable stop member 73 connected to the plate-shaped portion 74 provided with an adjustment knob 69 (FIG. 9).

Figure 12:
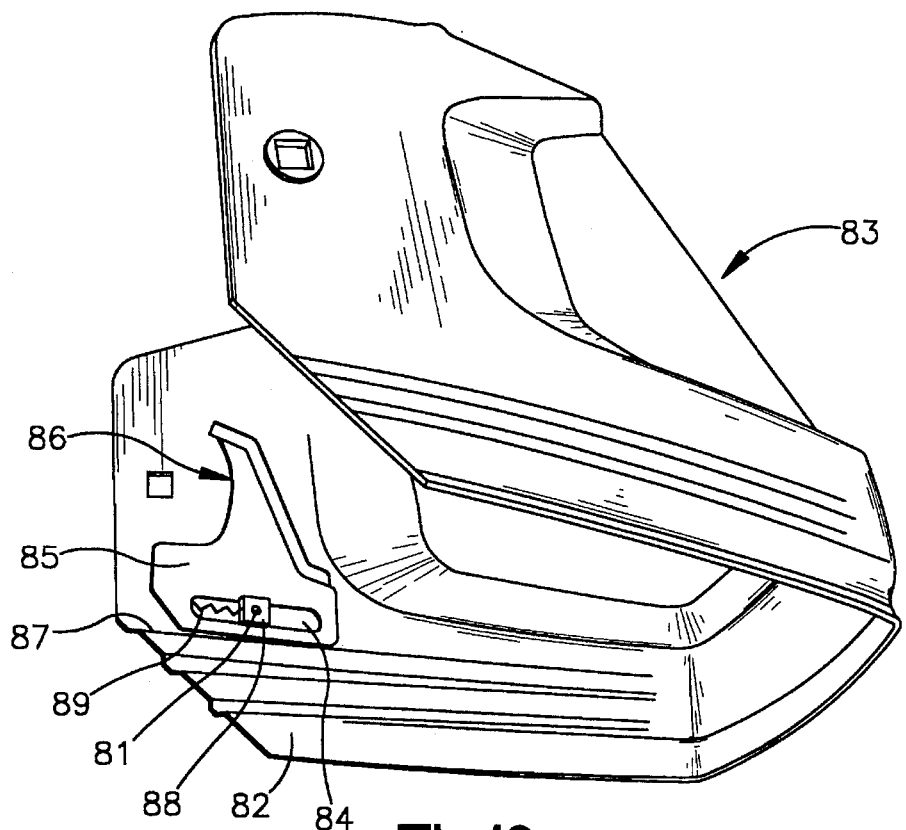
FIG. 12 shows a perspective view of the visor incorporating a still different embodiment of the stop assembly for the longitudinal adjustment of the visor.
Figure 13:
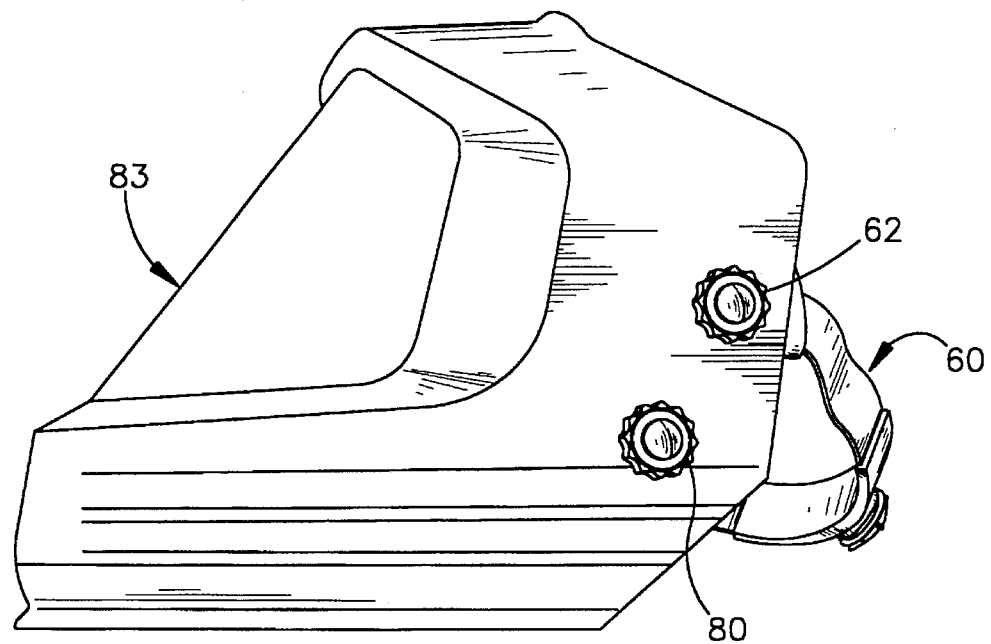
FIG. 13 shows a perspective view of the complete apparatus according to the invention incorporating the assembly for the longitudinal adjustment of the visor shown in FIG. 12.

In order to prevent the provision of a longitudinal slit in the lateral portion of the visor for displacing the threaded bolt of the adjustable stop member, a solution according to FIGS. 12 and 13 can be realized. Thereby, the position of the threaded bolt 81 provided with the adjustment knob 80 is fixed in the lateral portion 82 of the visor 83. Furthermore, for the same purpose, there is provided a longitudinal slit 84 in the plate-shaped portion 85 of the displaceable stop member 86; said displaceable stop member 86 is linearly guided along a rib 87 provided on the lateral portion 82 and is generally designed in the same manner as the corresponding stop member 73 in the embodiment according to FIGS. 10 and 11.

In order to fix the displaceable stop member 86 in the desired position, there is provided a clamping plate member 88 into which the threaded bolt 81 is screwed-in. This clamping connecting being released, a spring member 89 inserted for instance between the clamping member 88 and the plate-shaped member 85 forces the adjustable stop member 86 against the fixed stop member 70 (FIG. 11). The result is that the adjustment is effected by pivoting the visor 83 into the desired operational position. The support structure 60 and the means operable with the adjustment knob 62 for the displacement of the visor 83 in the viewing direction are designed in the same manner as shown and explained in and with reference to FIGS. 10 and 11.

Figure 14:
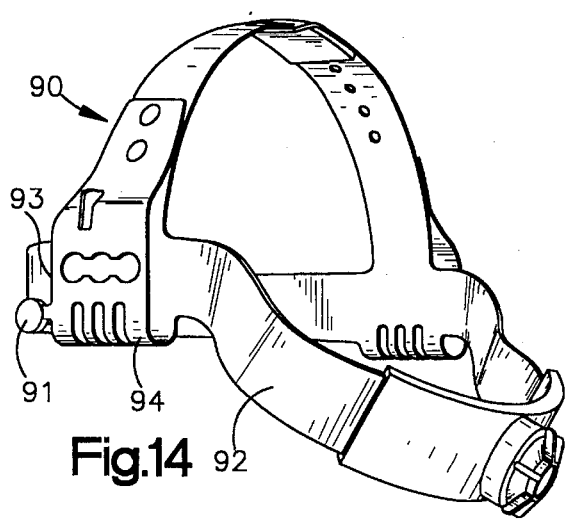
FIG. 14 shows a perspective view of the support structure incorporating a fixed stop member according to a further embodiment of the invention.
Figure 15:
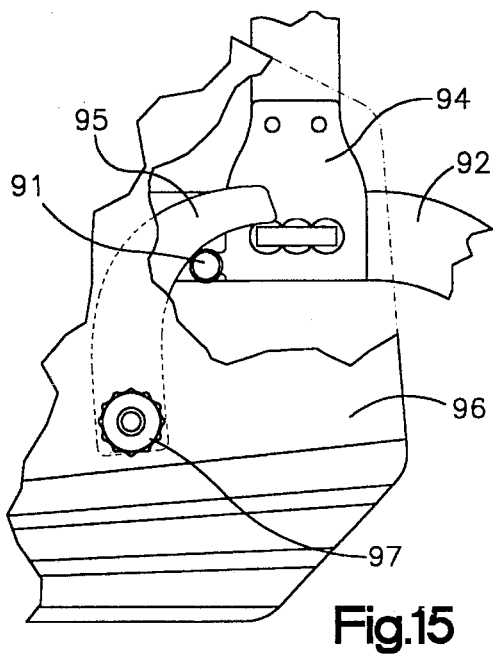
FIG. 15 shows a partial lateral view of the stop member assembly and the support structure according to FIG. 14.
Figure 16:
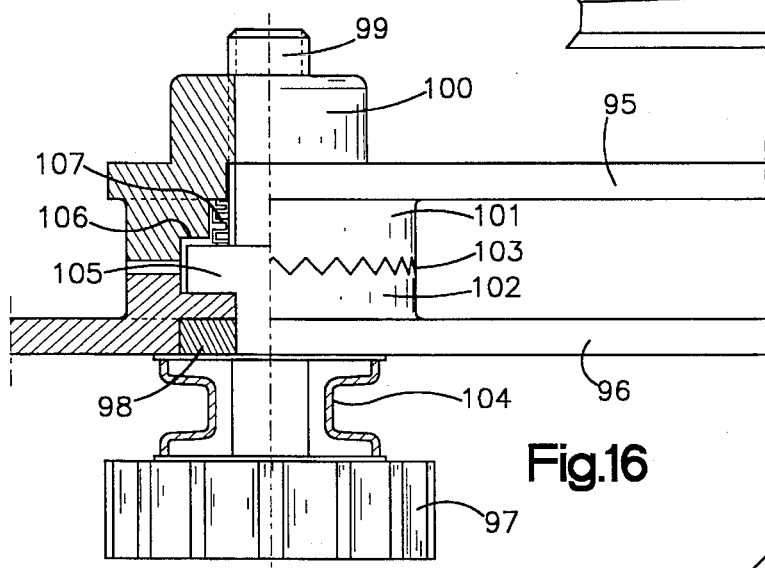
FIG. 16 shows the adjustment means for the stop member assembly according to FIG. 15 in a partially sectioned axial view.

A further embodiment of the invention is shown in FIGS. 14–16. This embodiment, on the one hand, is again designed such that no longitudinal slit is required in the lateral portion of the visor for the displacement of the adjustable stop member. On the other hand, this embodiment offers a solution for the case that the ear portion of the protected assembly can be provided with ear protection device.

As can be seen from FIGS. 14 and 15, the support structure 90 of the protecting assembly is designed essentially equal to the embodiment shown in FIG. 8. However, in contrary to the provision of the tab 71 and the land 72, a round pin 91 is provided here as a fixed stop member, said round pin being located in front of the frontal edge 93 of the outwardly protruding tape portion 94 at the forehead tape 92 and which protrudes outwardly therefrom in perpendicular direction. As an adjustable stop member, there is provided a rearwardly bent lever member 95; thereby, the design is such that the lever member 95 extends around the ear portion of the support structure 90 lying in the region of the outwardly protruding tape portion 94. The lever member 95 is pivotally received at the inner side of the lateral portion of the visor 96 and can be adjusted by means of an adjustment knob 97 into the desired position.

In FIG. 16 there is shown a practical embodiment of the adjustment means for the adjustable stop member in the form of the lever member 95. It is understood that this embodiment represents an example; it is within the skill of a person having knowledge in this art to vary the embodiment discussed herein below.

The lateral portion of the visor 96 comprises a bearing bush 98 pivotally receiving a threaded bolt 99 which also is displaceable in axial direction. The other end of the threaded bolt 99 is equipped with an adjustment knob 97 while the inner end of the threaded bolt 99 is screwed into a hub 100 of the lever member 95 serving as an adjustment abutment means.

The facing portions of the lever member 95 and of the lateral portion of the visor 96 are provided with hollow cylindrical portion 101 and 102, respectively, integrally formed therewith; these hollow cylindrical portions 101 and 102 are provided each with crown-shaped gear trains 103 engaging each other and, thereby, forming a positively engaging clutch member.

In order to keep the above-mentioned positively engaging clutch member in an engaged position, i.e. the parts 101 and 102 being positively connected to each other, a pressure spring 104 is provided and inserted between the lateral portion of the visor 96 and the adjustment knob 97; the result is that the lever member 95 is fixed in its preadjusted position.

The threaded bolt 99 comprises a collar 105 cooperating with a shoulder of the hollow cylindrical portion 101 such that, by loosening the screwed connection by means of the adjustment knob 97 and by axially displacing the above-mentioned threaded bolt by exerting a pressure onto the adjustment knob 97 against the force of the pressure spring 104, the positively engaging clutch member 101, 102 and 103 is released.

Furthermore, between the lever member 95 and the collar 105 located at the threaded bolt 99, there is provided a pressure spring 107 serving as a slip-clutch member; by rotating the adjustment knob 97, the slip-clutch member operates in such a way that the disengaged lever member is displaced into the desired stop position. If the adjustment knob 97 is released from the pressure exerted thereon, the positively engaging clutch member 101. 102, 103 engages again under the influence of the pressure spring 104 whereby the positive engagement can be further increased by tightening the screw connection.

Figure 17:
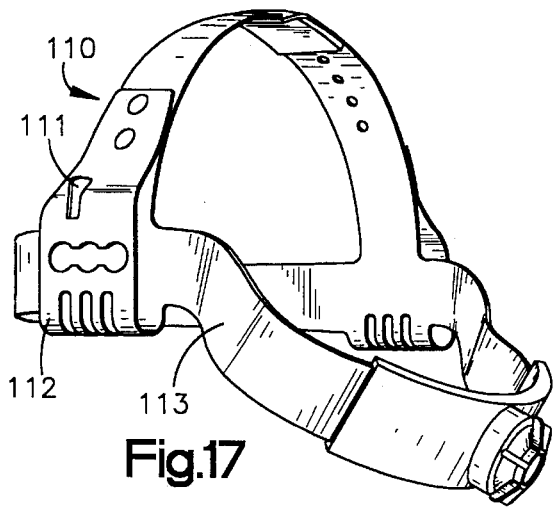
FIG. 17 shows a perspective view of the support structure incorporating a fixed stop member according to a further embodiment of the invention.
Figure 18:
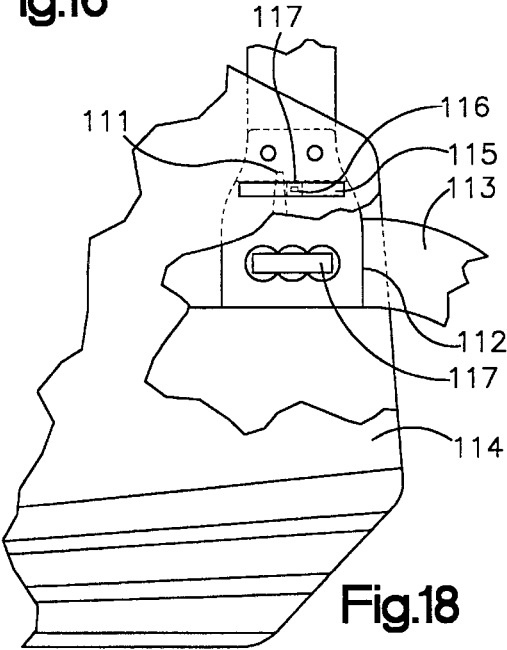
FIG. 18 shows a partial lateral view of the stop member assembly incorporating the support structure according to FIG. 17.

A still another, simpler embodiment of the abutment means, also providing for freeing the ear portion of the protective assembly, is shown in FIG. 17 and 18. In this embodiment, the support structure 110 comprises a fixed stop member 111 located in the upper portion of the outwardly protruding tape portion 112 of the forehead tape 113. At the same level, there is provided a longitudinal slit 115 in the corresponding lateral portion 114 of the visor. Displaceably received in this longitudinal slit 115, there is provided an adjustable abutment member in the shape of a pin 116; the bearing member 117 serving to support the above-mentioned pin 116 and the means for fixing the bearing member 117 by means of adjustment knob are not shown in detail. The longitudinal slit 115 essentially runs parallel to the longitudinal slit 117 in which the pivot axis of the visor is anchored.

What is claimed is:

1. A protective assembly for the protection of the human head from external detrimental effects, comprising:

a support structure adapted to be connected to the head of the person wearing the protective assembly;

a visor means through which a human wearing the protective assembly sees along a horizontal viewing axis, said visor means being pivotally connected to said support structure for swiveling from a lower operative position to an upper rest position; and means for adjusting and fixing the position of said visor means along said horizontal viewing axis and in said lower operative position, said means for adjusting and fixing the position of said visor means including actuating members for the operation of said means for adjusting and fixing the position of said visor means;

all said actuating members for the operation of said means for adjusting and fixing the position of said visor means being located at the outer side of the protective assembly and the visor means, respectively, such that they can be actuated in said lower operative position of the protective assembly to adjust and fix the position of said visor means along said horizontal viewing axis and in said lower operative position;

said support structure including a stiff-elastic forehead tape portion, said visor means being fixed to said forehead tape portion, said visor means including two lateral portions in operative connection with said support structure, each of said lateral portions being connected to said support structure by means of a releasable screw connection operating as a slip clutch member, said forehead portion of said support structure being provided with a radially outwardly protruding tape section located in the temple region of said support structure which serves as a basis portion for the determination of said releasable screw connection;

each of said radially outwardly protruding tape sections of said support structure and said lateral portions of said visor means each having a port-like aperture for receiving a threaded bolt forming the pivot axis for the visor, one of said port-like apertures, on each side of the visor, is in the shape of a longitudinal slit extending essentially parallel to the direction of viewing of the person wearing the protective assembly;

each of said longitudinal slits having, along its longitudinal extension, a plurality of snap-in recesses adapted to cooperate with an actuating knob member, said actuating knob member being located on said threaded bolt at the outside of said lateral portions of said visor in order to enable the wearer to positively fix the position of said visor with reference to said support structure in one of several predetermined positions defined by said snap-in recesses.

2. A protective assembly according to claim 1 in which three snap-in recesses are provided.

3. A protective assembly for the protection of the human head from external detrimental effects, comprising:

a support structure adapted to be connected to the head of the person wearing the protective assembly;

a visor means through which a human wearing the protective assembly sees along a horizontal viewing axis, said visor means being pivotally connected to said support structure for swiveling from a lower operative position to an upper rest position;

means for adjusting and fixing the position of said visor means along said horizontal viewing axis and in said lower operative position, said means for adjusting and fixing the position of said visor means including actuating members for the operation of said means for adjusting and fixing the position of said visor means;

all said actuating members for the operation of said means for adjusting and fixing the position of said visor means being located at the outer side of the protective assembly and the visor means, respectively, such that they can be actuated in said lower operative position of the protective assembly to adjust and fix the position of said visor means along said horizontal viewing axis and in said lower operative position, said support structure including a stiff-elastic forehead tape portion, said visor means being fixed to said forehead tape portion, said visor means including two lateral portions being in operative connection with said support structure, each of said lateral portions being connected to said support structure by means of a releasable screw connection operating as a slip clutch member, said forehead portion of said support structure being provided with a radially outwardly protruding tape section located in the temple region of said support structure which serves as a basis portion for the determination of said releasable screw connection; and a stop member means for determining said lower operative position of the pivotal visor means, said stop member means including a fixed stop member and an adjustable abutment member cooperating with said fixed stop member, said fixed stop member being located at said radially outwardly protruding tape section of said forehead portion of said support structure and said adjustable abutment member being located at the inner side of the related lateral portion of said visor means facing the outer side of said aforementioned lateral portion of said visor means.

4. A protective assembly according to claim 3 in which said adjustable abutment member has a means for displacement along a longitudinally extending path and is provided with a stop edge means running crosswise to said longitudinally extending path.

5. A protective assembly according to claim 3 in which said adjustable abutment member is fixed to said lateral portion of said visor means by means of a second releasable screw connection comprising a threaded bolt penetrating a port-like aperture provided in said lateral portion of said visor means as well as an actuating knob member received on said threaded bolt at the outer side of said lateral portion of said visor means.

6. A protective assembly according to claim 5 in which said threaded bolt is fixedly connected to the related lateral portion of said visor means, said related lateral portion of said visor means comprising a longitudinal slit along which said threaded bolt can be infinitely variably displaced and said threaded bolt being received in said longitudinal slit such that said threaded bolt cannot be rotated.

7. A protective assembly according to claim 5 in which the position of said threaded bolt is fixed in said port-like aperture provided in said lateral portion of said visor member and in which said adjustable abutment member comprises a longitudinal slit by means of which said abutment member is linearly displaceably and non-rotatably received on said threaded bolt.

8. A protective assembly according to claim 5 in which said adjustable abutment member includes spring means for forcing the adjustable abutment member against the fixed stop member once the connection between said adjustable abutment member and said fixed stop member is released.

9. A protective assembly according to claim 5 in which the position of the threaded bolt is fixed with reference to the port-like aperture in said lateral portion of said visor means and in which said adjustable abutment member is connected to said threaded bolt by means of a friction-clutch and to said lateral portion of said visor means by means of a positively engaging clutch means which can be disengaged by axially displacing said threaded bolt.

10. A protective assembly according to claim 3 in which said abutment and stop member means are located away from the ear portion of the support structure.

11. A protective assembly for the protection of the human head from external detrimental effects, comprising:
- a support structure adapted to be connected to the head of the person wearing the protective assembly;
- a visor means through which a human wearing the protective assembly sees along a horizontal viewing axis, said visor means being connected to said support structure for swivel movement between a lower operative position and an upper rest position and for movement along said horizontal viewing axis, relative to said support structure;
- adjustable stop means for stopping said visor means at said lower operative position;
- means for adjusting said adjustable stop means; and
- means for adjusting and fixing the position of said visor means along said horizontal viewing axis and in said lower operative position;
- said means for adjusting and fixing the position of said visor means and said means for adjusting said adjustable stop means including actuating members located at an outer side of the protective assembly for manual engagement and for manual operation by the person wearing the protective assembly to adjust the protective assembly while the person is wearing the protective assembly.

12. A protective assembly according to claim 11 in which said means for adjusting said adjustable stop means includes a bolt extending through an adjustment slit, said actuating members includes an actuating knob which is manually tightened on said bolt for locking said adjustable stop means in an adjustment position.

13. A protective assembly according to claim 11 in which said actuating members includes a first actuating knob which is manually operated for adjusting said adjustable stop means and a second actuating knob, spaced from said first actuating knob, which is manually operated for adjusting and fixing the position of said visor means along said horizontal viewing axis.

14. A protective assembly according to claim 11 in which said support structure comprises a stiff-elastic forehead tape portion, said visor means being fixed to said forehead tape portion.

15. A protective assembly according to claim 14 in which said visor means comprises two lateral portions being in operative connection with said support structure, each of said lateral portions being connected to said support structure by means of a releasable screw connection operating as a slip clutch member, the forehead portion of said support structure being provided with a radially outwardly protruding tape section located in the temple region of the support structure which serves as a basis portion for the determination of said releasable screw connection.

16. A protective assembly according to claim 15 in which each of said radially outwardly protruding tape sections of said support structure and said lateral portions of said visor means each comprise a port-like aperture for receiving a threaded bolt forming the pivot axis for the visor, one of said port-like apertures, on each side of the visor, is in the shape of a longitudinal slit extending essentially parallel to the direction of viewing of the person wearing the protective assembly.

17. A protective assembly according to claim 16 in which said port-like aperture in the shape of a longitudinal slit is located in said radially outwardly protruding tape section of said support structure.

18. A protective assembly according to claim 14, further comprising adjustment means for adapting the size of the support structure to the size of the head of the person wearing the protective assembly.

19. A protective assembly according to claim 18 in which said adjustment means comprise a self-locking adjustment assembly adjustable in the operative position of the protective assembly and adapted to adjust the circumferential dimension of the forehead tape portion of the support structure.

20. A protective assembly according to claim 19 in which said self-locking adjustment assembly for the adjustment of the forehead tape portion of the support structure is located at the neck portion of the latter.

21. A protective assembly according to claim 19 in which said forehead tape portion of said support structure comprises two free ends provided with a longitudinal slot, one of the edges of each slot being provided with a train of gears whereby the train of gears of the one slot is located on the opposite side as compared to the train of gears provided on the other slot if the said two free ends are placed one above the other.

22. A protective assembly according to claim 21 in which there is provided a clasp member surrounding said two free ends of said forehead tape portion, said clasp member comprising a gear wheel member rotatable about an axis, located in the interior of said clasp member and engaging the said two train of gears provided along the one edge of each two slots, said clasp member further comprising a friction-clutch means hampering the rotational movement of said gear wheel member as well as an actuating knob fixed to the outer side of said axis of said gear wheel member.

* * * * *